(12) United States Patent
Gustavsson et al.

(10) Patent No.: US 6,689,389 B2
(45) Date of Patent: *Feb. 10, 2004

(54) PHARMACEUTICALLY ACCEPTABLE STARCH

(75) Inventors: Nils Ove Gustavsson, Löddeköpinge (SE); Monica Jönsson, Bara (SE); Per Berdén, Malmö (SE); Timo Laakso, Campton (GB); Mats Reslow, Lund (SE)

(73) Assignee: Jagotec AG, Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/970,648

(22) Filed: Oct. 5, 2001

(65) Prior Publication Data

US 2002/0045745 A1 Apr. 18, 2002

Related U.S. Application Data

(60) Provisional application No. 60/260,491, filed on Jan. 8, 2001.

(30) Foreign Application Priority Data

Oct. 6, 2000 (SE) .............................. 0003616

(51) Int. Cl.$^7$ .............................. A61K 9/50; A61K 9/14; A61K 47/00; C08B 30/00
(52) U.S. Cl. .................... 424/499; 424/489; 424/488; 127/65; 514/778
(58) Field of Search ................. 424/489, 499, 424/488; 127/65; 514/778

(56) References Cited

U.S. PATENT DOCUMENTS

| | | | |
|---|---|---|---|
| 3,691,090 A | | 9/1972 | Kitajima et al. |
| 3,737,337 A | | 6/1973 | Schnoring et al. |
| 3,881,991 A | | 5/1975 | Kurimotor et al. |
| 3,909,288 A | * | 9/1975 | Powell et al. .................. 127/67 |
| 4,389,330 A | | 6/1983 | Tice et al. |
| 4,517,022 A | * | 5/1985 | Harvey ........................ 127/68 |
| 4,713,249 A | | 12/1987 | Schröder |
| 5,319,046 A | * | 6/1994 | Kozulic et al. ............. 526/304 |
| 5,407,609 A | | 4/1995 | Tice et al. |
| 5,424,302 A | | 6/1995 | Nitsch |
| 5,455,342 A | | 10/1995 | Redding, Jr. |
| 5,470,582 A | | 11/1995 | Supersaxo et al. |
| 5,578,709 A | | 11/1996 | Woiszwillo et al. |
| 5,622,657 A | | 4/1997 | Takeda et al. |
| 5,654,010 A | | 8/1997 | Johnson et al. |
| 5,667,808 A | | 9/1997 | Johnson et al. |
| 5,753,234 A | | 5/1998 | Lee et al. |
| 5,776,885 A | | 7/1998 | Orsolini et al. |
| 5,945,528 A | | 8/1999 | Sommermeyer et al. |
| 5,959,102 A | * | 9/1999 | Wasserman et al. .......... 127/34 |
| 5,981,719 A | | 11/1999 | Woiszwillo et al. |
| 6,010,574 A | * | 1/2000 | Jeffcoat et al. ............... 127/65 |
| 6,248,268 B1 | * | 6/2001 | Cook ........................ 530/373 |

FOREIGN PATENT DOCUMENTS

| | | |
|---|---|---|
| EP | 0008241 A2 | 2/1980 |
| EP | 0 213 303 A2 | 3/1987 |
| EP | 0 540 582 B1 | 8/1994 |
| EP | 0 688 429 B1 | 2/1998 |
| EP | 0 330 180 B2 | 3/1999 |
| JP | 11302156 | 11/1999 |
| WO | WO 90/13780 A1 | 11/1990 |
| WO | WO 93/21008 A1 | 10/1993 |
| WO | WO 94/12158 A1 | 6/1995 |
| WO | WO 96/10042 A1 | 4/1996 |
| WO | WO 97/14408 A1 | 4/1997 |
| WO | WO 99/00425 A1 | 1/1999 |
| WO | WO 99/20253 A1 | 4/1999 |

OTHER PUBLICATIONS

US 5,849,884, 12/1998, Woiszwillo et al. (withdrawn)

"Formation and Isolation of Spherical Fine Protein Microparticles Through Lyophilization of Protein—Poly(ethylene glycol) Aqueous Mixture", Takahiro Morita et al., Pharmaceutical Research, vol. 17, 11, 2000, pp. 1367 to 1373.

Protein encapsulation into biodegradable microsphere by a novel S/O/W encapsulation method using poly(ethylene glycol) as a protein micronization adjuvant, Takahiro Morita et al., Journal of Controlled Release, 69 (2000) pp. 435–444.

Artursson et al., "Characterization of Polyacryl Starch Microparticles as Carriers for Proteins and Drugs," Journal of Pharmaceutical Sciences, vol. 73, No. 11, pp. 1507–1513, (1984).

Franssen et al., "A Novel Preparation Method for Polymeric Microparticles Without the Use of Organic Solvents," International Journal of Pharmaceutics, vol. 168, pp. 1–7 (1998).

Fu et al., "Visual Evidence of Acidic Environmental Within Degrading Poly(lactic–co–glycolic acid) (PLGA) Microspheres" Pharmaceutical Research, vol. 17, No. 1, pp. 100–106 (2000).

Laakso et al., "Biodegradable Microspheres IV: Factors Affecting the Distribution and Degradation of Polyacryl Starch Microparticles," Journal of Pharmaceutical Sciences, vol. 75, No. 10, pp. 962–967 (1986).

Laakso et al., "Biodegradable Microspheres X: Some Properties of Polyacryl Starch Microparticles Prepared from Acrylic Acid–Esterified Starch," Journal of Pharmaceutical Sciences, vol. 76, No. 12, pp. 935–939 (1987).

(List continued on next page.)

Primary Examiner—Shengjun Wang
(74) Attorney, Agent, or Firm—Burns, Doane, Swecker & Mathis, L.L.P.

(57) ABSTRACT

Production of purified, parenterally administrable starch by washing starch containing more than 85% amylopectin in order to remove surface-localized proteins, lipids and endotoxins, dissolving the starch in aqueous medium, molecular weight reduction by shearing, and optionally removal of residual water-soluble proteins, preferably by anion exchange chromatography.

Purified starch and microparticles based on such starch.

42 Claims, No Drawings

OTHER PUBLICATIONS

Schröder, "Crystallized Carbohydrate Spheres as a Slow Release Matrix for Biologically Active Substances," *Biomaterials*, vol. 5, pp. 100–104 (1984).

Schröder, "Crystallized Carbohydrate Spheres for Slow Release and Targeting," *Enzymology*, vol. 112, No. 9, pp. 116–128 (1985).

Stenekes et al., "The Preparation of Dextran Microspheres in an All–Aqueous System: Effect of the Formulation Parameters on Particle Characteristics," *Pharmaceutical Research*, vol. 15, No. 4, pp. 557–561 (1998).

Stjärnkvist et al., "Biodegradable Microspheres XIII: Properties of the Crosslinking Chains in Polyacryl Starch Microparticles," *Journal of Pharmaceutical Sciences*, vol. 78, No. 1, pp. 52–56 (1989).

Agersø et al., "Plasma Concentration of hGH and anti–hGH Antibodies After Subcutaneous Administration of hGH for 3 Weeks to Immunosuppressed Pigs," *J. Pharmacol Toxicol* No. 41, pp. 1–8 (1999).

Johnson et al., "A Month–Long effect From a Single Injection of Microencapsulated Human Growth Hormone," *Nature Medicine*, vol. 2, No. 7 pp. 795–799 (1996).

Putney, "Encapsulation of Proteins for Improved Delivery," Current Opinion in *Chemical Biology*, Nol. 2, pp. 548–552 (1998).

"Clean Package Insert," Nutropin Depot (somatropin(rDNA origin) for injectable suspension, Genentech, Inc., 1 DNA Way, South San Francisco, CA 940–4990, pp. 1–6 (Dec. 13, 1999).

* cited by examiner

PHARMACEUTICALLY ACCEPTABLE STARCH

This application claims priority under 35 U.S.C. §§119 and/or 365 to Application No. 0003616-0 filed in Sweden on Oct. 6, 2000 and U.S. Provisional Application No. 60/260,491, filed Jan. 8, 2001; the entire content of which is hereby incorporated by reference.

TECHNICAL FIELD

The present invention relates to starch of a quality such that it is pharmaceutically acceptable for parenteral administration to a mammal, especially a human. In particular, the said starch can be used for production of microparticles containing a biologically active substance for controlled release thereof.

BACKGROUND TO THE INVENTION

Many drugs have to be administered parenterally, in particular by injection, since they are either subjected to degradation or are insufficiently absorbed when they are given, for example, orally or nasally or by the rectal route. A drug preparation intended for parenteral use has to meet a number of requirements in order to be approved by the regulatory authorities for use on humans. It must therefore be biocompatible and biodegradable and all used substances and their degradation products must be non-toxic. In addition, particulate drug preparations intended for injection have to be small enough to pass through the injection needle, which preferably means that they should be smaller than 200 $\mu$m. The drug should not be degraded in the preparation to any great extent during production or storage thereof or after administration and should be released in a biologically active form with reproducible kinetics.

One class of polymers which meets the requirements of biocompatibility and biodegradation into harmless end products is the linear polyesters based on lactic acid, glycolic acid and mixtures thereof. These polymers will also hereinafter be referred to as PLGA. PLGA is degraded by ester hydrolysis into lactic acid and glycolic acid and has been shown to possess excellent biocompatibility. The innocuous nature of PLGA can be exemplified, moreover, by the approval by the regulating authorities, including the US Food and Drug Administration, of several parenteral delayed release preparations based on these polymers.

Parenterally administrable delayed release products currently on the market and based on PLGA include Decapeptyl™ (Ibsen Biotech), Prostap SR™ (Lederle), Decapeptyl® Depot (Ferring) and Zoladex® (Zeneca). The drugs in these preparations are all peptides. In other words, they consist of amino acids condensed into a polymer having a relatively low degree of polymerization and they do not have any well-defined three-dimensional structure. This, in turn, usually allows the use of relatively harsh conditions during the production of these products. For example, extrusion and subsequent size-reduction can be utilized, which techniques would probably not be allowed in connection with proteins, since these do not, generally speaking, withstand such stringent conditions.

Consequently, there is also a need for controlled release preparations for proteins. Proteins are similar to peptides in that they also consist of amino acids, but the molecules are larger and the majority of proteins are dependent on a well-defined three-dimensional structure as regards many of their properties, including biological activity and immunogenicity. Their three-dimensional structure can be destroyed relatively easily, for example by high temperatures, surface-induced denaturation and, in many cases, exposure to organic solvents. A very serious drawback connected with the use of PLGA, which is an excellent material per se, for delayed release of proteins is therefore the need to use organic solvents to dissolve the said PLGA, with the attendant risk that the stability of the protein will be compromised and that conformation changes in the protein will risk leading to an immunological reaction in the patient, which can produce both a loss of therapeutic effect, through the formation of inhibitory antibodies, and toxic side effects. Since it is extremely difficult to determine with certainty whether a complex protein has retained its three-dimensional structure in every respect, it is very important to avoid exposing the protein to conditions which might induce conformation changes.

Despite intense efforts aimed at modifying the PLGA technology in order to avoid this inherent problem of protein instability during the production process, progress within this field has been very slow, the main reason probably being that the three-dimensional structures for the majority of proteins are far too sensitive to withstand the manufacturing conditions used and the chemically acidic environment formed with the degradation of PLGA matrices. The scientific literature contains a large number of descriptions of stability problems in the manufacture of microspheres of PLGA owing to exposure to organic solvents. As an example of the acidic environment which is formed upon the degradation of PLGA matrices, it has recently been shown that the pH value in a PLGA microsphere having a diameter of about 40 $\mu$m falls to 1.5, which is fully sufficient to denature, or otherwise damage, many therapeutically usable proteins (Fu et al, Visual Evidence of Acidic Environment Within Degrading Poly(lactic-co-glycolic acid) (PLGA) Microspheres, Pharmaceutical Research, Vol. 17, No. 1, 2000, 100–106). Should the microspheres have a greater diameter, the pH value can be expected to fall further owing to the fact that the acidic degradation products have more difficulty in diffusing away and the autocatalytic reaction is intensified.

A number of attempts to solve problems caused by exposure of the biologically active substance to a chemically acidic environment during the biodegradation of the microsphere matrix and organic solvents in the manufacturing process have been described. In order to avoid an acidic environment during the degradation, attempts have been made to replace PLGA as the matrix for the microspheres by a polymer which produces chemically neutral degradation products, and in order to avoid exposing the biologically active substance to organic solvents, either it has been attempted to manufacture the microspheres in advance and, only after they have been processed and dried, to load them with the biologically active substance, or attempts have been made to exclude or limit the organic solvent during manufacture of the microspheres.

By way of example, highly branched starch of relatively low molecular weight (maltodextrin, average molecular weight about 5,000 Da) has been covalently modified with acryl groups for conversion of this starch into a form which can be solidified into microspheres and the obtained polyacryl starch has been converted into particulate form by radical polymerization in an emulsion with toluene/chloroform (4:1) as the outer phase (Characterization of Polyacryl Starch Microparticles as Carriers for Proteins and Drugs, Artursson et al, J Pharm Sci, 73, 1507–1513, 1984). Proteins were able to be entrapped in these microspheres, but the manufacturing conditions expose the biologically active substance to both organic solvents and high shearing forces in the manufacture of the emulsion. The obtained microspheres are dissolved enzymatically and the pH can be expected to be kept neutral. The obtained microspheres are not suitable for parenteral administration, especially repeated administrations, for a number of reasons. Most important of all is the incomplete and very slow biodegradability of both the starch matrix (Biodegradable Microspheres IV. Factors Affecting the Distribution and Degradation of Polyacryl Starch Microparticles, Laakso et al, J Pharm Sci 75, 962–967, 1986) and the synthetic polymer chain which cross-links the starch molecules. (Stjärnkvist P., Laakso T. and Sjöholm I. (1989) Biodegradable microspheres. XII: Properties of the crosslinking chains in polyacryl starch microparticles, J. Pharm. Sci. 78, 52–56). Moreover, these microspheres are far too small, <2 µm in diameter, to be suitable for injection in the tissues for sustained release, since tissue macrophages can easily phagocytize them. Attempts to raise the degradation rate and the degree of degradation by introducing a potentially biodegradable ester group in order to bond the acryl groups to the highly branched starch failed to produce the intended result and even these polyacryl starch microspheres were biodegraded far too slowly and incompletely over reasonable periods of time (BIODEGRADABLE MICROSPHERES: Some Properties of Polyacryl Starch Microparticles Prepared from Acrylic acid Esterified Starch, Laakso and Sjöholm, 1987 (76), pp. 935–939, J Pharm Sci.)

Manufacture of starch microspheres with the use of non-chemically-modified starch using an oil as the outer phase has been described (U.S. Pat. No. 4,713,249; Schröder, U., Crystallized carbohydrate spheres for slow release and targeting, Methods Enzymol, 1985 (112), 116–128; Schröder, U., Crystallized carbohydrate spheres as a slow release matrix for biologically active substances, Bio-materials 5:100–104, 1984). The microspheres are solidified in these cases by precipitation in acetone, which leads both to the exposure of the biologically active substance to an organic solvent and to the non-utilization, during the manufacturing process, of the natural tendency of the starch to solidify through physical cross-linking. This leads, in turn, to microspheres having inherent instability, since the starch, after resuspension in water and upon exposure to body fluids, will endeavour to form such cross-links. In order for such a water-in-oil emulsion to be obtained, high shear forces are required and the microspheres which are formed are far too small to be suitable for parenteral sustained release.

EP 213303 A2 describes the production of microspheres of, inter alia, chemically unmodified starch in two-phase aqueous systems, utilizing the natural capacity of the starch to solidify through the formation of physical cross-links, and the immobilization of a substance in these microspheres for the purpose of avoiding exposure of the biologically active substance to organic solvents. The described methodology, in combination with the starch quality which is defined, does not give rise to fully biodegradable particles. Neither are the obtained particles suitable for injection, particularly for repeated injections over a longer period, since the described starch quality contains far too high quantities of foreign vegetable protein.

That starch is, in theory, a very suitable, perhaps even ideal, matrix material for microparticles has been known for a long time, since starch does not need to be dissolved in organic solvents and has a natural tendency to solidify and since there are enzymes within the body which can break down the starch into endogenic and neutral substances, ultimately glucose, and since starch, presumably owing to the similarity with endogenous glycogen, has been shown to be non-immunogenic. Despite intense efforts, starch having properties which enable manufacture of microparticles suitable for parenteral use and conditions which enable manufacture of fully biodegradable microparticles under mild conditions, which allow sensitive, biologically active substances, such as proteins, to become entrapped, has not been previously described.

Starch granules from natural sources contain impurities, such as starch proteins, which makes them unsuitable for parenteral administration. In the event of unintentional depositing of insufficiently purified starch, such as can occur in operations where many types of operating gloves are powdered with stabilized starch granules, very serious secondary effects can arise. Neither are starch granules intrinsically suitable for repeated parenteral administrations, for the reason that they are not fully biodegradable within acceptable time spans.

Starch microspheres made of acid-hydrolyzed and purified starch have been used for parenteral administration to humans. The microspheres were made by chemical cross-linking with epichlorohydrin under strongly alkaline conditions. The chemical modification which was then acquired by the starch leads to reduced biodegradability, so that the microspheres can be fully dissolved by endogenic enzymes, such as α-amylase, but not converted fully into glucose as the end product. Neither the manufacturing method nor the obtained microspheres are suitable for the immobilization of sensitive proteins, nor is such acid-hydrolyzed starch, which is essentially based on hydrolyzed amylose, suitable for producing either fully biodegradable starch microspheres or starch microspheres containing a high load of a biologically active substance, such as a protein.

Hydroxyethyl starch (HES) is administered parenterally to humans in high doses as a plasma substitute. HES is produced by starch granules from starch consisting broadly exclusively of highly branched amylopectin, so-called "waxy maize", being acid-hydrolyzed in order to reduce the molecular weight and being subsequently hydroxyethylated under alkaline conditions and acid-hydrolyzed once more to achieve an average molecular weight of around 200,000 Da. After this, filtration, extraction with acetone and spray-drying are carried out. The purpose of the hydroxyethylation is to prolong the duration of the effect, since non-modified amylopectin is very rapidly degraded by α-amylase and its residence time in the circulation is around 10 minutes. HES is not suitable for the production of fully biodegradable microspheres containing a biologically active substance, since the chemical modification leads to a considerable reduction in the speed and completeness of the biodegradation and results in the elimination of the natural tendency of the starch to solidify through the formation of non-covalent cross-linkings. Moreover, highly concentrated solutions of HES become far too viscous to be usable for the production of microparticles. The use of HES in these high doses shows that parenterally usable starch can be manufactured, even though HES is not usable for the manufacture of microspheres without chemical cross-linking or precipitation with organic solvents.

WO 99/00425 describes the use of heat-resistant proteolytic enzymes with wide pH-optimum to purify starch granules from surface-associated proteins. The obtained granules are not suitable for parenteral administration, since they still contain the starch proteins which are present within the granules and there is a risk that residues of the added proteolytic enzymes will be left in the granules. Neither are the granules suitable for the manufacture of parenterally administrable starch microspheres in two-phase aqueous systems, since they have the wrong molecular weight distribution to be able to be used in high enough concentration, even after being dissolved, and, where microspheres can be obtained, they are probably not fully biodegradable.

The use of shearing to modify the molecular weight distribution of starch, for the purpose of producing better starch for the production of tablets, is described in U.S. Pat. No. 5,455,342 and WO 93/21008. The starch which is obtained is not suitable for parenteral administration owing to the high content of starch proteins, which might be present in denatured form after the shearing, and neither is the obtained starch suitable for producing biodegradable starch microspheres for parenteral administration or for use in two-phase aqueous systems for the production of such starch microspheres. Shearing has also been used to manufacture hydroxyethylstarch, as is disclosed in WO 96/10042. However, for similar reasons such hydroxyethylstarch is not either suitable for parenteral administration or for the production of microspheres as referred to.

A process for the production of parenterally administrable starch preparations having the following features would therefore be particularly desirable:
 a process by means of which a substantially fully biodegradable and biocompatible starch can be produced, which is suitable for administering parenterally and upon whose degradation chemically neutral endogenic substances are formed;
 a parenterally acceptable starch which is suitable for the production of substantially fully biodegradable starch microparticles.

Objects such as these and other objects are achieved by means of the invention defined below.

DESCRIPTION OF THE INVENTION

According to a first aspect of the present invention, this provides a process for the production of a starch which is pharmaceutically acceptable for parenteral administration, especially by means of injection, to a mammal, including a human.

An especially relevant application of such a starch is for the production of parenterally administrable, substantially completely biodegradable starch microparticles, into which a biologically active substance can be incorporated with high yield and under such mild conditions, in a two-phase aqueous system, for example, that its biological activity is retained. The expression parenteral administration is primarily understood to require that such microparticles must have a suitable size distribution, purity and biodegradability and be biocompatible. High yield is intended to mean that the starch must be capable of forming such highly concentrated solutions that the biologically active substance that is to be incorporated into the starch microparticles formed cannot diffuse out into surrounding phases, or into the interface between the phases, to any significant extent, and that the starch solution used solidifies into microparticles with sufficient rapidity but in a controlled manner. It has surprisingly emerged that the process according to the present invention permits the production of such starch.

Starch from natural sources contains some impurities that are not acceptable for parenteral administration to humans, in particular various particulate materials, proteins and endotoxins. The process according to the present invention makes it possible to purify the starch from these constituents that are unacceptable for parenteral use. The difficulty with such a process is that the said constituents are numerous, and their content may vary depending on natural seasonal variations, and that they have widely differing characteristics, such as solubility, physical form, location etc. To develop such a process for the production of a starch, which is also suitable for the production of microparticles in two-phase aqueous systems and which is acceptable to the registration authorities, is even more complex. Through a combination of the choice of basic starch and certain specific purification stages it has, however, proved surprisingly possible, according to the present invention, to produce such a starch.

The process according to the invention briefly consists in taking starch with a high amylopectin content, washing this in order to eliminate surface-localized proteins, lipids, and endotoxins, reducing the molecular weight of the starch by shearing, and preferably also eliminating residual, ab initio non-surface localized proteins.

More precisely, the process according to the present invention comprises:
 a) starting from starch in solid form, especially particles, for example granules, and with an amylopectin content in excess of 85 percent by weight,
 b) subjecting said solid starch to washing(s) under conditions such that proteins, lipids and endotoxins surface-localized on the starch are dissolved whilst the starch remains undissolved, and separating the starch from the dissolved material,
 c) causing the washed starch obtained from step b) to dissolve in an aqueous medium, and
 d) subjecting the starch solution to molecular weight reduction by shearing, so that a molecular weight distribution is obtained in which at least 80% of the material is within the range of 10–10,000 kDa.

The starch used as a starting material in the process according to the present invention must therefore be largely amylopectin-based, that is to say the proportion of amylose must be small. An especially preferred amylopectin content in this context is at least 95 percent by weight, more preferably at least 98 percent by weight, the percentage contents being expressed throughout as dry weight of starch. Such a starch can be obtained commercially from a number of suppliers or can be produced by means of processes well known in this technical field. An especially preferred starch is a so-called waxy maize starch, in particular a native or acid-hydrolyzed one. Such starch is processed commercially on a large scale for a number of applications, using well-known processes. An example of a native waxy maize starch that can be used is Cerestar 04201, and an example of an acid-hydrolyzed starch is Cerestar C* Gel 06090. These types of starch are not suitable for parenteral administration as such, or for the production of starch microparticles for parenteral administration due, among other things, to insufficient purity and insufficient biodegradability, but are therefore treated according to the present invention for processing into pharmaceutically acceptable starch.

Starch particles or starch granules having a mean diameter in the range of 5–25 μm, based on weight distribution, are preferably used as the starting starch in the process according to the present invention.

Before subjecting the starting starch material to the washing or washings in step b), non-starch material is preferably removed therefrom. This may suitably be done by sieving and/or sedimentation. Material that is larger than the starch particles can in this context be removed by wet-sieving, for example, whilst material that is smaller than the starch particles is removed by sedimentation, for example. This may appropriately involve the removal of non-starch material larger than 40 μm and preferably also material which is smaller than 5 μm.

If raw starch is in fact studied under an optical microscope, small quantities of fibrous material can normally be observed, and the raw starch material may also be expected to contain plant residues, grit and other particles of an undefined nature. Particles such as microorganisms and residues thereof, which form a sediment more slowly than starch granules, may be removed, for example, by repeated sedimentation. It is advantageous in this way to obtain an homogeneous population of starch particles as basic material for the further purification steps, whilst at the same time eliminating the risk of accidentally introducing various particulate materials with a size greater than the particle size of the starch in question. The initial treatment also results in improved filtering capability in subsequent steps.

Since the starting starch is a relatively cheap material, losses can be tolerated in this initial step in order thereby to obtain a high degree of purity and a reliable purification method. Since the initial steps in the removal of non-starch material are also time-consuming and the material to be purified is a good substrate for bacterial growth, it is also important that the processes in question be carried out under conditions which do not permit the growth of microorganisms and which at the same time must be acceptable for the production of an injectable material. Within this technical field there is a large number of well-known solutions to this very problem, such as the use of bacteriostatic substances, temperatures that do not allow the growth of microorganisms, or other conditions that inhibit the growth of microorganisms. One very simple measure is adjustment of the pH value, for example to a level of approximately 11.

The washing in step b) is generally performed under alkaline conditions, preferably at a pH value in the range of approximately 11–14 and in one or more stages, the conditions being chosen so as not to dissolve the starch granules. An alkali metal hydroxide, particularly sodium hydroxide, is preferably chosen as alkali. Preferably at least one stage is used for dissolving water-soluble proteins, lipids and endotoxins, and at least one stage with solvents for dissolving more sparingly soluble material, especially proteins, that is to say those which are not soluble in water alone. One material of this type is the protein zein. In their native state all the different variants of zein are insoluble in water and dilute salt solutions, which is a characteristic that defines prolamines in general, and since the starting starch very often contains zeins in significant quantities (approximately half of the protein content in maize), it is essential in such a case that they be eliminated.

It is primarily a question therefore of using an aqueous solvent with the ability to dissolve zein, by means of which more sparingly soluble proteins can be removed. The solvent must naturally also be acceptable for the production of parenterally administrable starch. The washing step b), or modifications thereof, can remove many different classes of non-starch materials.

The said solvent with the ability to dissolve zein is preferably selected from aqueous solutions of monovalent or divalent alcohols and ketones, preferably alkanols or alkylene glycols containing a total of up to 4 carbon atoms or dialkyl ketones with a total of up to 5 carbon atoms.

Suitable alkanols are ethanol and isopropanol, especially ethanol, and suitable alkylene glycols are ethylene glycol and propylene glycol. A suitable dialkyl ketone is acetone.

The following is a suitable procedure for the initial steps of the process according to the invention. Starch is suspended in an aqueous solution, preferably water for injection, and a typically useable concentration is approximately 10 kg of starch per 80 kg of water. The aqueous solution is adjusted to a suitable pH value, that is to say for dissolving the substances that are to be removed whilst at the same time seeking to avoid dissolution of starch, a suitable value being approximately 11, for example. Sodium hydroxide solution, preferably in a relatively low concentration, is also used in order to achieve the said pH value. At the same time it is also advantageous if the addition is performed slowly whilst stirring thoroughly. According to an especially preferred embodiment, the suspension is pumped, for example with a peristaltic pump, to a vibrating screen mesh with a nominal pore size of 40 μm, for example, for the aforementioned filtering.

The starch particles are resuspended to form a homogeneous suspension, for example with a large paddle, and are normally allowed to settle for 1–24 hours, preferably 3–14 hours, most preferably at room temperature, and the supernatant is carefully decanted or drawn off. This should be repeated a number of times, for example at least three times. In addition the particles can also be allowed to stand in the final alkaline solution whilst stirring for a longer period, for example at least twenty-four hours, in order to further ensure elimination of alkali-soluble proteins.

Actual washing of the starch particles is thereafter performed under alkaline conditions, which also detoxify endotoxins. In this procedure, various bases, for example sodium hydroxide, potassium hydroxide and thioglycolate may be used, alone or in combination. The conditions are generally selected so that the proteins that are to be removed remain soluble, whilst the starch particles remain insoluble, after which the washing solution can be separated off by suitable means, for example through sedimentation or filtering, preferably under accelerated conditions. This washing procedure can then be repeated until the intended result has been achieved. A suitable contact time for the starch particles in the alkaline solution is at least 2 hours, more preferably at least 4 hours. The washed granules are separated from the washing liquid each time, for example by means of filtering or centrifuging in a basket centrifuge. The alkali concentration is selected so that an effective concentration is obtained without the starch particles dissolving. The pH value is preferably one in the range of 11.5–13. A typical concentration is 0.0125 M where sodium hydroxide is used, which gives a pH value of approx. 12. According to the most preferred embodiment, a basket centrifuge and an alkali hydroxide concentration of approx. 0.0125 M are used. The first washing is preferably carried out in the basket centrifuge itself, in order, for example, to thereby reduce the concentration of substances used in earlier stages. In subsequent stages the particles are then resuspended in the washing liquid, which is then introduced into the basket centrifuge for separation. A typical ratio of washing liquid to starch is approximately 5:1, for example 50 liters of washing liquid per 10 kg of starch. Three washings are normally sufficient.

If so desired, the efficiency of the washing can be qualitatively verified by means of gel electrophoresis, for example under denaturing conditions, or quantified, for example by amino acid analysis of the starch.

If the basic starch contains material such as proteins, lipids and endotoxins etc., which do not dissolve in a solely alkaline aqueous solution, the said material is removed by subjecting the starch to washing with the said solvent having the ability to dissolve zein. The composition of the solution is here selected so that the material in question is dissolved without the starch entering into solution. The right conditions for this are usually ones in which the input pH value in the aqueous phase is in the range of 12.5–13.5. An especially preferred composition is an equimolar mixture of ethanol and water-based alkali solution, for example water for injection with the addition of 0.1 M sodium hydroxide. The formed suspension of starch and used washing solution is suitably stirred for a period of between 4 hours and 12 hours, for example at room temperature. Washing may thereafter be performed, for example, in a basket centrifuge equipped with a spray nozzle for final washing with water for injection.

Following the said washing stages, the purified starch particles may either be subjected immediately to the subsequent steps of the process according to the invention or be stored in the form of an intermediate product, before the final steps are carried out. They may be stored in refrigerated or dry form, for example. Drying can be carried out by suitable means, preferably after washing with ethanol. Alternatively, the purified starch can be stored in amorphous, non-granular form, to which it can be converted by dissolving under heat, either refrigerated or in dry form.

According to current specifications and methods of analysis, the abovementioned washings with alkali metal hydroxide are entirely satisfactory for the starch particles. However, if the requirements are increased in the future, for example through the development of even more sensitive methods of analysis, the washing according to step b) can be supplemented by washing with a thioglycolate solution in order to remove more sparingly soluble proteins. Thioglycolate has proved to be effective in removing sparingly soluble proteins, such as keratins, from a basic starch material of the abovementioned type. Thioglycolate is also acceptable for parenteral use and can be washed away from the particles. Caution must be exercised, however, when using thioglycolate, since it is an eye and skin irritant and has an unpleasant odour, but these factors are entirely manageable.

Before the dissolved starch is subjected to shearing, any residual particulate non-starch material is preferably removed by filtering the solution. This may be done, for example, by combining a pre-filter with a pore size of approx. 20 $\mu$m or less followed by a filter with a pore size of 0.5 $\mu$m or 0.45 $\mu$m in series. For dissolving the starch, water is preferably used that is acceptable for the manufacture of starch for parenteral use, most preferably water for injection. Dissolution is generally performed at elevated temperature, for example a temperature of at least 80° C., and a typical concentration is 1–25%, for example approx. 10%. Pumping through the filters in question may be done in any suitable way. The pumping is most preferably performed at excess pressure, which is built up in stages and which does not exceed 3 bar, which is limited by the mechanical strength of the filter. Examples of possible filters are Ultipor GF 2+20 $\mu$m (Pall) and Fluorodyne II (Pall). A suitable dimension is 20 inches and cartridge filters are to be preferred. The filtering is carried out at elevated temperature in order to avoid the precipitation of starch, but the temperature must at the same time naturally not exceed what the filter material will tolerate. In the event of any filter becoming clogged, the procedure may be continued after changing to a new filter.

The molecular weight distribution of the starch is then reduced by shearing, which is preferably performed in a high-pressure homogenizer. The reduction of the molecular weight and the molecular weight distribution that are achieved are primarily a function of the pressure used and the number of passages through the homogenizer. What levels of these factors ought to be used in each individual case can easily be determined by the person skilled in the art by means of experimentation at a certain starch concentration. When carrying out the shearing, the molecular weight distribution of the starch can be determined by the method described below after each passage through the homogenizer, in order to ensure that the desired molecular weight distribution is obtained. By means of the process according to the invention, it is possible to obtain the desired molecular weight distribution without a large proportion of unwanted, low molecular material being formed. Furthermore, a significantly narrower molecular weight distribution can be obtained than can be achieved using other methods. Since the shearing procedure can lead to fragmentation and possibly partial dissolution of unwanted particulate material, it is preferable to remove such unwanted particulate material, for example bacteria residues, before shearing, as discussed above.

A suitable homogenizer for use in the process according to the invention is Rannie model 12.56H (APV Denmark). The decision of which homogenizer to use is based on its ability to reduce the molecular weight distribution of the starch and its suitability from the point of view of cleaning, for example, since it will be operating in a process for the production of a parenterally administrable material.

The molecular weight distribution obtained by shearing is preferably such that at least 80% of the material falls within the range of 100–4000 kDa, more preferably 200–1000 kDa and most preferably 300–600 kDa.

The molecular weight distribution can be determined by a number of different methods known per se. The most preferred is based on gel filtering with detection on the basis of the refractive index and detection by means of so-called Multiple Angle Laser Light Scattering (MALLS). Suitable equipment is the DAWN-F Multi Angle Laser Light Scattering detector, and a suitable program for the collection of data and determination of the average molecular weight and the polydispersity is ASTRA 2.11a, and a suitable computer program for evaluation of the molecular weight range is EASI 6.00 (all from Wyatt Technology Corporation).

The shearing is preferably performed at a pressure in excess of 1200 bar, for example in the range of 1200–1500 bar, but should be specifically determined for each type of homogenizer, since the particular design of the apparatus is also of significance. The maximum pressure for the apparatus stated above is suitably used, which is equal to 1500 bar, and in practice it is generally the maximum pressure for the apparatus used that sets the upper limit. It is possible to obtain the same molecular weight distribution whether the homogenization is carried out in the form of discrete passages or by recirculation. A typical starch concentration by homogenization is approx. 10%, and a suitable medium is water for injection, as has been discussed above.

For producing a starch with a still greater margin of safety for parenteral administration, water-soluble proteins are also removed from the starch. Such removal is most preferably performed after the shearing step d) but can also be performed before the same.

According to one embodiment of the process according to the invention the removal of water-soluble proteins is also accomplished by subjecting the starch solution to ion exchange chromatography.

According to the most preferred embodiment, anion exchange chromatography is used in order to eliminate negatively charged water-soluble proteins. Unlike the proteins and other contaminants that were removed in step b)

and which were primarily made up of material occurring on the surface of the starch particles, with ion exchange chromatography it is primarily a matter of removing proteins that were originally located inside the starch particles and hence largely inaccessible in the initial purification. The quantity of ion exchange material that is needed for this purification can, if necessary, easily be titrated experimentally. Generally, however, it has been shown that larger quantities of ion exchange material should preferably be used than have been conventionally employed. By using more ion exchange material than has hitherto been common, elution of the various constituents from the ion exchange material may result in higher concentration of the said constituents in the starch than is normally the case. In this case an ion exchange material should therefore be selected which only leads to elution of constituents which are acceptable for parenteral use. One example of a suitable ion exchange material is Q-Sepharose (Pharmacia Amersham). The process can be performed both using a column and by way of a batch process. In the latter case the ion exchange material is suspended in the starch solution, which is then separated off by suitable means, for example by filtering.

Suitable conditions for ion exchange chromatography are normally stated in the instructions issued by the manufacturer and in the scientific literature. It is generally possible to achieve the same results using reasonable differences in process parameters for this technique, and these conditions will therefore only be illustrated by typical, non-limiting examples. Suitable conditions for the use of Q-Sepharose are, for example, a 10 mM sodium carbonate buffer, pH 9.8, at approx. 45° C. If necessary, a stronger buffer can be used, but in that case a desalination stage ought to be incorporated after the chromatography. The quantity of ion exchange material should be at least 0.4 ml, preferably at least 0.8 ml, sedimented bed volume of ion exchange material per g of starch, in the order of magnitude, for example, of 0.4–1.1, calculated as swollen volume in the buffer in question, at room temperature, per kg dry weight of starch. The ion exchange material should be washed or regenerated by a conventional method. A suitable method, however, is treatment with 1 M sodium hydroxide for, say, 1 hour at room temperature followed by rinsing with two bed volumes of water for injection and rinsing with a total of two bed volumes of 2 M sodium chloride, spread over four additions, for example. This procedure can thereafter be repeated once. Rinsing is then performed with water for injection until the conductivity is less than 2 mS/cm and equilibration is then performed twice with a bed volume of 100 mM sodium carbonate buffer, pH 9.8, and thereafter with 10 mM sodium carbonate buffer, pH 9.8, until both the pH and conductivity have been stabilized. The ion exchange may be performed, for example, by a batch process which lasts at least 4 and up to 48 hours at 45° C. For practical reasons it is often elected to carry out the ion exchange over one night. The ion exchange is suitably performed under gentle stirring, so that the integrity of the ion exchange material is preserved. The ion exchange mass is then separated from the starch solution by suitable means, for example by introducing the suspension into a chromatography column with suitable outlet filter. The pH value of the starch solution is then neutralized. Where volatile or unstable buffer substances are used, the pH value should be reduced a few pH units below neutral, so as to prevent excessively alkaline conditions occurring during subsequent spray drying, for example, when the buffer substance may be broken down or convert into a gaseous phase.

According to another embodiment of the process claimed the removal of water-soluble proteins is accomplished by means of an electrophoresis operation. Such an operation can be performed in accordance with known principles forelectrophoresis, which for instance generally means that the starch is subjected to said electrophoresis in the form of a gel.

After the removal of water-soluble proteins, filtering is preferably performed to remove any particulate contamination generated during the same. There are a large number of suitable filters commercially available for this purpose. A suitable configuration is a 5 $\mu$m pre-filter and a 0.5 $\mu$m final filter. Suitable dimensions are 20 inches for pre-filters and 10 inches for final filters. Examples of suitable filters are Profile Star (Pall) and Star Clear (Pall), which is positively charged.

The purified starch is suitably subjected to a final drying step before being stored. An especially preferred method of drying in this respect is spray drying, although other methods known per se are also suitable, for example freeze-drying or vacuum drying. In spray drying the conditions should be selected so that the material is dried sufficiently without unwanted secondary reactions occurring due to excessively high temperature and/or too alkaline a pH value. Typical temperatures for use in this context are approx. 200° C. as inlet temperature and approx. 120° C. as outlet temperature. The outlet temperature can easily be controlled by means of the pumping rate for the starch solution.

The starch can be kept for a long time if it is stored in dark, dry conditions at a temperature that does not exceed normal room temperature. Before the starch is used for the production of microspheres intended for parenteral use, it is dissolved, for example in water for injection, and sterilized. The preferred method of sterilization is autoclaving. Other methods of sterilization, such as sterile filtration, are also possible.

The purity of the starch can be determined by methods well known per se. In order to obtain a qualitative assessment, gel electrophoresis is preferably used under denaturing conditions with subsequent staining. In order to obtain more quantitative data, the nitrogen content can be determined, for example by amino acid analysis, elemental analysis or by means of nitrogen-selective detectors. Amino acid analysis is preferred, since this provides quantitative data relating to the protein content of the starch and this is the most important factor for the usefulness of the starch. The method can reduce the content of amino acid nitrogen to 50 ppm, suitably below 20 ppm, preferably to less than 10 ppm, more preferably to less than 5 ppm, or even below 2 ppm, which provides a good safety factor, especially in repeated parenteral administrations, and which is on a par with or lower than the content of amino acid nitrogen in hydroxyethyl starch, which is used parenterally as plasma expander and which in daily dosage may exceed the maximum intended for starch particles by at least 100 times, based on kg of body weight. After producing antibodies to the input protein constituents, which is itself already described in the scientific literature, it is possible to use sensitive immunological methods for quantifying the said constituents.

According to a second aspect of the present invention, this also provides a novel pharmaceutically acceptable starch. This is characterized in that it
a) has an amylopectin content in excess of 85 percent by weight, in which the molecular weight of the said amylopectin has been reduced, preferably by shearing, so that at least 80 percent by weight of the material is within the range of 10–10000 kDa,
b) has a purity of at most 50 $\mu$g amino acid nitrogen per gram dry weight of starch, preferably at most 20 $\mu$g, more preferably at most 10 μg and most preferably at most 5 μg, amino acid nitrogen per gram dry weight of starch,
c) can be dissolved in a concentration exceeding 25 percent by weight in water.

The expression "can be dissolved in water" is intended to mean dissolution by a conventional method for starch, which generally involves heating, for example to at least 80° C., and also dissolving in buffered aqueous solution.

According to another aspect of the present invention, this provides a pharmaceutically acceptable starch which
a) has an amylopectin content in excess of 85 percent by weight, in which the molecular weight of the said amylopectin has been reduced, preferably by shearing, so that at least 80 percent by weight of the material lies within the range of 10–10000 kDa,
b) has a purity of at most 50 μg amino acid nitrogen per gram dry weight of starch, preferably at most 20 μg, more preferably at most 10 μg and most preferably at most 5 μg, amino acid nitrogen per gram dry weight of starch,
c) lacks covalently bonded additional chemical groups of the type that occur in hydroxyethyl starch.

The expression "lacks additional covalently bonded chemical groups of the type that occur in hydroxyethyl starch" is generally intended to mean that the starch only contains those groups that occur in natural starch and have not been modified as in hydroxyethyl starch, for example.

In addition, the starch according to any of the abovementioned aspects preferably exhibits the ability to gel naturally in vitro.

According to another embodiment, the abovementioned starch exhibits the ability to form microparticles in an emulsion system, especially a two-phase aqueous system.

Another embodiment relates to starch with an endotoxin content of less than 25 EU/g, and a further embodiment relates to starch containing fewer than 100 microorganisms per g, more preferably fewer than 10 microorganisms per g.

Still further preferable embodiments of the starch are the following.

A starch which can be dissolved in water in a concentration exceeding 30%, preferably exceeding 40%, and more preferably exceeding 45%, by weight.

A starch which remains in solution at a temperature of at most 60° C., preferably 20–45° C., especially 30–37° C., for a period sufficiently long to allow combining with a substance that is temperature sensitive and/or unstable in organic solvents, especially a protein. Said combining is preferably performed at conditions which are able to retain the bioactivity of said substance.

A starch which when dissolved in water solidifies at a temperature of 1–55° C., especially 4–37° C.

A starch which solidifies when exposed to an initial temperature of 1–10° C., especially about 4° C., and subsequently to a temperature of 20–55° C., preferably 25–40° C., especially about 37° C.

For other especially preferred embodiments of this starch, reference is made to the embodiments which have been described above in connection with the process according to the invention, for which reason these need not be repeated here.

The main area of application of the novel starch is for the production of essentially completely biodegradable microparticles. It may, however, naturally also be used in other contexts where pharmaceutically acceptable starch may be relevant, for example for the production of HES (hydroxyethyl starch).

According to a third aspect or the present invention, however, this also provides microparticles based on starch as carrier for a biologically active substance, especially for parenteral administration, preferably by way of injection, to a mammal, including a human, in which the said starch is the starch that has been defined above.

Such microparticles preferably have a mean particle diameter in the range of 10–200 μm, preferably 20–100 μm, especially 20–80 μm. The term microparticles is therefore used as general designation for particles of a certain size known in the art. One type of microparticles is that of microspheres which have a substantially spherical shape, although the term microparticle may include deviations from such an ideal spherical shape. The known term microcapsule is also covered by the expression microparticle in accordance with the prior art.

A preferred embodiment of such microparticles is represented by those particles which exhibit the ability to be dissolved by enzymatic action in vitro and eliminated from biological tissue in vivo.

It will be apparent from what has been stated that a biologically active substance of special interest is a protein, but the invention is naturally also applicable in principle to any active substance that can be used for parenteral administration, for example (poly)peptides, (poly) nucleotides, plasmids and DNA. The invention is, however, of special interest in those cases in which problems of sensitivity and instability exist.

Examples of biologically active substances of the abovementioned type are growth hormone, erythropoietin, interferon ($\alpha$, $\beta$, $\gamma$-type), vaccine, epidermal growth hormone, Factor VIII, LHRH-analog, insulin, macrophage-colony-stimulating factors, granulocyte-colony-stimulating factors and interleukin.

Usable biologically active substances of non-protein pharmaceutical type may be selected from the following groups: anti-tumor drugs, antibiotics, anti-inflammatory drugs, antihistamines, sedatives, muscle relaxants, anti-epileptics, antidepressants, anti-allergy preparations, bronchodilators, cardiotonic drugs, anti-arrhythmic drugs, vasodilators, antidiabetic drugs, anticoagulants, haemostatics, narcotics and steroids.

With regard to the structure of microspheres, microcapsules or microparticles in general and the various methods that exist for producing these, reference is made to the known literature. The starch according to the invention, however, has proved to be especially suitable for the production of microparticles of the type that is described in the Swedish patent application entitled "Microparticles" filed concurrently with the present patent application. For details of this, reference is therefore made to said patent application.

The invention will now be further explained by means of the following, non-limiting examples. In these, as in the rest of the text, unless otherwise stated the percentages quoted relate to percentage by weight.

EXAMPLES

Example 1

Production of Pure Highly Branched Starch of Low Molecular Weight

Starch (waxy maize. National Starch) in granular form was suspended in water, produced by reverse osmosis, in a concentration of 5 kg per 50 liters of water. Sodium hydroxide was added until the pH value was 11. The suspension was stirred for half an hour and the liquid was separated from the granules by centrifuging in a basket centrifuge. This was repeated twice. The granules were washed with water and kept in 5 liters of ethanol over the weekend. The granules were then washed twice with 10 liters of 70% ethanol and then with water. The material was then suspended in water at 60° C. and then poured into 40 liters of water and dissolved, partially with the aid of a jet mixer whilst stirring, the solution forming a foam, which lay on the surface. The molecular weight distribution was then reduced by shearing (Microfluidizer 110 T. Microfluids Corp.) at 1500 bar, in a total of 15 passages. The starch solution was heated to 70° C. and filtered through a pre-filter (Pall profile II 20 µm, 10-inch diameter and Pall Starclear 0.5 µm, positively charged, 10-inch diameter), and spray-dried (200° C. inlet temperature, approx. 122–127° C. outlet temperature). In total, approximately 3 kg of starch was obtained with an av. mol. wt. of 1,930 kDa.

The raw starch contained approx. 0.052% of nitrogen, determined by means of elemental analysis, and the starch obtained contained approx. 0.022% nitrogen. Both the raw starch and the cleaned starch contained <10 microorganisms per gram. However, 30 microorganisms per gram were found in an intermediate stage, which shows the need for conditions that prevent microorganisms from increasing in the course of the process. The amino acid nitrogen value was 56.53 µg/g of starch (dry weight) and the starch passed the test for pyrogens according to Ph. Eur. $2^{nd}$ Ed. after parenteral administration to rabbits. After repeated parenteral administration of the starch intraperitoneally to guinea-pigs in order to permit induction of an immune response, followed by intravenous administration of the starch in order to detect any anaphylactic reactions, the starch was found to have no capacity to induce an anaphylactic reaction. The starch obtained thus fulfils the requirements for a raw material for the production of a parenteral preparation.

Example 2

Production of Starch for Parenteral Use

A starch suspension (waxy maize starch, Cerestar* gel 06090) with a concentration of 10 kg in 75 liters of water for injection was prepared under stirring. Once a homogeneous suspension had been formed, 0.25 M of sodium hydroxide solution was added until a pH value of 11.0±0.2 was obtained, and it was thereafter topped up with more water for injection to a total volume of 80 liters. The suspension was pumped through a wet sieve at a rate of flow of approximately 520 ml/min. The starch suspension was left to settle in Müller vessels overnight, and next day the top solution was decanted by means of a siphon until 18 liters of the suspension remained. After topping up with 72 liters of water for injection the pH value was still found to be at least 10.5, so that there was no need to add further sodium hydroxide solution. The suspension was allowed to stand for 12 hours, after which the top liquid was decanted. This was repeated once more with settlement overnight. The starch granules were then washed with 0.0125 M sodium hydroxide solution in water for injection, first by rinsing the filter cake in the basket centrifuge with 45 liters of the solution and then by suspension in the solution and elimination of the solution by centrifuging in the basket centrifuge. The latter stage was repeated once more. The starch granules were then leached for four hours with an equimolar solution of 0.1 M sodium hydroxide and ethanol, after which the solution was separated off by means of a basket centrifuge. This leaching was repeated once, after which the starch granules were washed twice with 40 liters of water for injection. The pH value of the starch suspension was adjusted to 6.4±1 with 1 M hydrochloric acid and washed with 50 liters of water for injection in the basket centrifuge. The starch was transferred to a freezer for storage. The quantity obtained was determined as 7.32 kg of dry starch.

Of the starch granules obtained, 3.7 kg were taken and suspended in 1.76 kg of water for injection and then transferred to 27.62 kg of water for injection, which was heated to 100° C. After stirring, the starch was visually judged to be dissolved. The starch was filtered through a 20-inch pre-filter with pore sizes of 20 and 2 µm and a 0.45 µm filter until the flow was considered to be too low. At this point <5% of the starch solution remained. The molecular weight distribution of the starch was adjusted by shearing at a set pressure of 1500 bar according to the manufacturer's instructions. The flow at this pressure was 2.25 liters/minute. The aim was to allow the solution to pass through the homogenizer enough times for the average molecular weight to become 350 kDa-500 kDa. In total 9 passages were performed. The pH value of the starch solution was then adjusted by the addition of sodium hydrogen bicarbonate to a final concentration of 10 mM and adjustment of the pH value by 0.5 to 9.8. Residual proteins were then eliminated by ion exchange chromatography on a Q-Sepharose FF (Pharmacia) using a total bed volume of 3.7 liters. The ion exchange material had previously been allowed to swell and was washed with a bed volume of 1 M sodium hydroxide, then with two bed volumes of water for injection, and thereafter under flow with 3 times the half bed volume of 2 M sodium chloride solution. This entire sequence was repeated once more, after which the ion exchange mass was rinsed with water for injection until the conductivity was less than 2 mS/cm. Equilibration was performed with two bed volumes of 100 mM sodium carbonate, pH 9.8, and then with 10 mM sodium hydrogen carbonate until both the pH value and the conductivity had been stabilized. The ion exchange material and the starch were mixed and kept at 45° C. under slow stirring with a top-mounted anchor agitator for approximately 15 hours, and the ion exchange mass was then separated by collecting in a chromatography column, the bed volume being kept at approximately 1.5 times the sedimentable bed volume required to keep the pressure below 3 bar. After adjusting the pH value to 6.4, the ion exchange starch was filtered through a pre-filter (PALL filter cartridge Profile star 5 µm, 20-inch diameter) and a final filter (PALL filter cartridge Starclear 0.5 µm, 10-inch diameter) after these had been preheated by pumping hot water for injection beforehand. Finally the starch solution was spray-dried with an inlet temperature of 200° C. and an outlet temperature of 120–125° C.

The protein content of the starch was determined by amino acid analysis. The raw starch contained approx. 137 ppm of amino acid nitrogen, after wet sieving it contained approx. 124 ppm, after sedimentation 61 ppm amino acid nitrogen, after treatment at pH 10.5 64 ppm amino acid nitrogen, after the third washing with 0.0125 M sodium hydroxide solution 54 ppm amino acid nitrogen, after washing with alkali/ethanol wash 52 ppm amino acid nitrogen, and after washing with water for injection 50 ppm amino acid nitrogen. On triple sampling after ion exchange chromatography, the following values were obtained for amino acid nitrogen; 1.8, 3.0 and 0.4 µg/g dry weight of starch.

The average molecular weight was determined by gel filtration combined with refractive index and MALLS detection and found to be 584 kDa after 3 passages, 508 kDa after 6 passages, and 434 kDa after 9 passages. The endotoxin content was determined as <25 EU/g using a Limbulus amebocyte nephelometric method of analysis validated for starch (Associates of Cape Cod Int Inc).

What is claimed is:

1. A process for the production of a starch having a purity of at most 50 ug amino acid nitrogen per gram dry weight of starch and an endotoxin content of less than 25 EU/g and containing fewer than 100 microorganisms per gram, said starch being pharmaceutically acceptable for injection into a human being, which comprises
- a) starting from starch in solid form and with an amylopectin content in excess of 85 percent by weight, expressed as dry weight of starch,
- b) subjecting said solid starch to washing(s) under conditions such that proteins, lipids and endotoxins surface-localized on the starch as well as more sparingly soluble proteins are dissolved while the starch remains undissolved, and separating the starch from the dissolved material, said washings comprising a washing with an aqueous alkaline solution for dissolving said water-soluble proteins, lipids and endotoxins and a washing with an aqueous solvent with the ability to dissolve zein for dissolving said more sparingly soluble proteins;
- c) causing the washed starch obtained from step b) to dissolve in an aqueous medium,
- d) subjecting the starch solution to a molecular weight reduction by shearing such that a molecular weight distribution is obtained in which at least 80 percent by weight of the material lies within the range of 10–10000 kDa; and
- e) removing residual water-soluble proteins from the starch by subjecting the starch solution to ion exchange chromatography, said ion exchange chromatography being performed either before or after the shearing step d)

wherein the starch is pharmaceutically acceptable for injection into a human being.

2. A process according to claim 1, which comprises removing said water-soluble proteins after performing step d) to reduce the molecular weight of the starch.

3. A process according to claim 1, which comprises removing said water-soluble proteins before performing step d) to reduce the molecular weight of the starch.

4. A process according to claim 1, in which said starch is waxy maize starch.

5. The process of claim 4, wherein the waxy maize starch is native or acid-hydrolyzed starch.

6. A process according to claim 1, in which step a) is undertaken using starch particles with an average diameter in the range 5–25 $\mu$m, based on weight distribution.

7. A process according to claim 1, in which the washing in step b) is performed under alkaline conditions and in one or more stages.

8. A process according to claim 7, in which the washing or washings in step b) is/are performed at a pH value in the range of 11–14.

9. The process of claim 8, wherein the washing or washings in step b) are performed in two stages with a first stage using aqueous alkali solution at pH 11.5–13 and a second stage which is performed under conditions in which the input value in the aqueous phase is in the range of 12.5–13.5.

10. The process of claim 7, wherein the washing in step b) is performed using sodium hydroxide as an alkali.

11. A process according to claim 1, in which the solvent with the ability to dissolve zein is selected from aqueous solutions of monovalent or divalent alcohols and ketones, preferably alkanols or alkylene glycols containing a total of up to 4 carbon atoms or dialkyl ketones with a total of up to 5 carbon atoms.

12. A process according to claim 11, in which the solvent is selected from aqueous solutions of ethanol, isopropanol, ethylene glycol, propylene glycol and acetone.

13. A process according to claim 12, in which the solvent is an aqueous ethanol solution.

14. A process according to claim 1, in which the dissolution in step c) is carried out so that a starch solution is obtained with a concentration in the range of 1–25%.

15. A process according to claim 1, in which the dissolution in step c) is carried out in water acceptable for production of starch for parenteral use.

16. The process of claim 15, wherein the water is acceptable for injection.

17. A process according to claim 1, in which the shearing in step d) is carried out so that a molecular weight distribution is obtained in which at least 80% of the material is in the range of 100–4000 kDa.

18. The process of claim 17, wherein at least 80% of the material is in the range of 200–1000 kDa.

19. The process of claim 17, wherein at least 80% of the material is in the range of 300–600 kDa.

20. A process according to claim 1, in which the shearing in step d) is carried out in a high-pressure homogenizer.

21. A process according to claim 20, in which the shearing is carried out at a pressure in excess of 1200 bar.

22. The process of claim 21, wherein the pressure is in the range of 1200–1500 bar.

23. A process according to claim 1, wherein the ion exchange chromatography is anion exchange chromatography.

24. A process according to claim 1, in which prior to the washings in step b) residual particulate non-starch material is removed from the starting starch.

25. A process according to claim 24, in which residual particulate non-starch material that is larger than the starch particles is removed by wet sieving and residual particulate non-starch material that is smaller than the starch particles is removed by sedimentation.

26. A process according to claim 24, in which residual particulate non-starch material that is larger than 40 $\mu$m is removed.

27. The process of claim 26, wherein residual particulate non-starch material that is smaller than 5 $\mu$m is also removed.

28. The process of claim 24, wherein the residual particulate non-starch material is removed from the starting starch by sieving and/or sedimentation.

29. A process according to claim 1, in which prior to the shearing in step d) any residual particulate non-starch material is removed by filtering of the solution and optionally thereafter through a 0.5 $\mu$m filter.

30. The process of claim 29, wherein the residual particulate non-starch material is removed by filtering of the solution through a 20 $\mu$m filter.

31. A process according to claim 1, in which the solution obtained from the shearing in step d) is subjected to filtering to remove any particulate contamination generated during said shearing.

32. The process of claim 31, wherein the filtration is carried out with a 5 $\mu$m filter.

33. A process according to claim 1, in which after the removal of residual water-soluble proteins from the starch, filtering is carried out to remove any particulate contamination.

34. The process of claim 33, wherein the filtration is carried out through a 5 $\mu$m pre-filter and a 5 $\mu$m filter.

35. A process according to claim 1, in which at least 0.4 ml of sedimented bed volume of ion exchange material per gram of starch is used in the ion exchange chromatography.

36. The process of claim 35, wherein at least 0.8 ml of sedimented bed volume of ion exchange material per gram of starch is used in the iron exchange chromatography.

37. A process according to claim 1, in which the purified starch is subjected to a final drying stage.

38. A process according to claim 37, wherein the final drying stage is carried out by means of spray drying.

39. A process according to claim 1, in which the washing in step b) comprises washing with a thioglycolate solution to remove sparingly soluble proteins.

40. The process of claim 1, wherein the solid form is a particle.

41. The process of claim 40, wherein the particle is a dried granule.

42. The process of claim 1, wherein amylopectin content is in excess of 98 percent by weight, expressed as dry weight of starch.

* * * * *